United States Patent [19]

Scheler et al.

[11] Patent Number: 5,406,137
[45] Date of Patent: Apr. 11, 1995

[54] CIRCUIT ARRANGEMENT FOR EVALUATING THE SIGNAL OF A CAPACITIVE MEASURING SENSOR

[75] Inventors: Bernd Scheler, Bad Orb; Dieter Ehlers, Mühlheim, both of Germany

[73] Assignee: Honeywell AG, Offenbach, Germany

[21] Appl. No.: 99,792

[22] Filed: Jul. 30, 1993

[30] Foreign Application Priority Data

Aug. 7, 1992 [DE] Germany .............. 42 26 137.6

[51] Int. Cl.⁶ ............................................. G05F 1/10
[52] U.S. Cl. ..................................... 327/509; 307/650; 327/227; 327/113
[58] Field of Search ............... 307/296.6, 310, 308, 307/271, 273; 328/4; 73/61.46, 24.04; 324/663, 664, 669, 670, 676

[56] References Cited

U.S. PATENT DOCUMENTS

| | | | |
|---|---|---|---|
| 4,112,317 | 9/1978 | Everswick | 307/308 |
| 4,237,420 | 12/1980 | Ebihara et al. | 307/223 |
| 4,282,480 | 8/1981 | Fujito et al. | 324/670 |
| 4,287,470 | 9/1981 | Fabian et al. | 324/620 |
| 4,330,718 | 5/1982 | Kinomoto et al. | 328/4 |
| 4,563,634 | 1/1986 | Lehle | 307/271 |
| 5,046,859 | 9/1991 | Yamaguchi | 307/310 |
| 5,132,631 | 7/1992 | Klopfenstein et al. | 324/663 |

OTHER PUBLICATIONS

Technical note 134, "Capacitive humidity sensor for consumer applications", Philips, 7 pages.
Technical information 063, "Capacitive humidity sensor", 15 pages (20 Nov. 1980).

Primary Examiner—Timothy P. Callahan
Assistant Examiner—Dinh Le
Attorney, Agent, or Firm—Charles L. Rubow

[57] ABSTRACT

A capacitive humidity sensor circuit in which a one-shot circuit produces pulses having a pulse duration determined by the capacitance of a capacitive sensing element, the one-shot circuit being triggered by the trailing edges of pulses in a pulse train produced by a multivibrator. The multivibrator is adjustable to produce a pulse train of variable repetition rate independent of the value of the measured parameter. The pulses produced by the one-shot circuit are integrated to produce a voltage indicative of the time average value of the pulses, the voltage being supplied to an amplification and offset compensation circuit whose output signal is used to adjust the supply voltage to the multivibrator so as to effectively achieve compensation for nonlinear response of the capacitive sensing element to increasing relative humidity.

10 Claims, 3 Drawing Sheets

CIRCUIT ARRANGEMENT FOR EVALUATING THE SIGNAL OF A CAPACITIVE MEASURING SENSOR

BACKGROUND OF THE INVENTION

The present invention relates generally to circuits of the type in which the output signal of multivibrator apparatus is controlled by a variable capacitance sensor element, and more particularly to such a circuit in which the capacitance value of the sensor element determines the width of a pulse produced at a repetition rate independent of the capacitance value.

It is well known that the capacitance of an element may be affected by certain environmental parameters, e.g., humidity. This characteristic has long been used as a basis for a variety of sensors and sensing systems. Such a sensor or system typically includes a capacitive sensor element specifically designed and constructed to enhance its response to the parameter of interest, and an electrical circuit, such as a bridge network, responsive to variations in capacitance of the sensor element.

Another approach to generating a sensed parameter signal from the capacitance of a variable capacitance sensor element is shown in the following documents:

(1) VALVO report TI 790423, "Sensor zur Messung der relativen Luftfeuchte", Philips GmbH, 11 pages (2) Technical note 134, "Capacitive humidity sensor for consumer applications", Philips, 7 pages (3) Technical information 063, "Capacitive humidity sensor", 15 pages (20 Nov. 1980)

The circuit shown and described in these documents basically uses two multivibrators, of which one generates a rectangular wave whose characteristics are proportional to the capacitance of a reference capacitor. This multivibrator is coupled to the second multivibrator in such a way that a rectangular wave produced by the second multivibrator is synchronized with that produced by the first multivibrator, the rectangular wave generated by the second multivibrator having a pulse duration which proportional to the capacitance of a sensing capacitor. The rectangular wave outputs of both multivibrators are logically combined to produce a pulse train in which the pulse duration corresponds to the difference in the pulse durations of the signals produced by the two multivibrators.

Yet another approach to utilizing the capacitance of a sensing capacitor for indicating an environmental parameter is shown in U.S. Pat. No. 4,563,634 issued to E. Lehle on Jan. 7, 1986. This approach involves a single multivibrator having cross coupled branches, one of which includes a capacitive sensor having a capacitance $C_{sens}$, and the other of which includes a reference capacitor having a capacitance $C_{ref}$. An output signal taken from each of these branches is averaged by a separate resistor-capacitor network, the average values being supplied to opposing inputs of a differential amplifier. The differential amplifier provides an output signal whose value, $U_A$, is given by the following equation:

$$U_A = \frac{C_{sens} - C_{ref}}{C_{sens} + C_{ref}}$$

The output signal of the differential amplifier is also used to vary the voltage supplied to the reference and sensing capacitors to partially compensate for the non-linear response which is inherent in capacitor based sensors and sensing systems. However, this compensation does not completely linearize the circuit response. In addition, the described circuit arrangement precludes use of the differential amplifier for providing independent offset compensation since both input terminals of the differential amplifier are required for receiving the two averaged output signals from the multivibrator.

SUMMARY OF THE INVENTION

The invention is a circuit employing a capacitive sensing element and means for evaluating the signal therefrom, such means including a multivibrator arranged to produce a pulse train whose characteristics are independent of a parameter being measured, the output of the multivibrator being supplied to a one-shot circuit so as to trigger pulses therefrom in synchronism with pulses in the pulse train produced by the multivibrator. The duration of the pulses produced by the one-shot circuit is determined by the capacitance of the capacitive sensing element, the output of one-shot circuit alone being supplied to signal processing circuitry which produces a signal indicative of the sensed parameter.

The processing circuitry may include a differential amplifier of which a first input receives a voltage corresponding to the time average value of the pulse train produced by the one-shot circuit, and of which a second input is connected in a network which, in conjunction with a variable power supply, provides a linearizing charging voltage to the capacitive sensing element. The network also provides for independent offset compensation and output impedance matching.

Accordingly, the applicants have achieved a circuit for evaluating the signal of a capacitive measuring sensor which overcomes various disadvantages of known prior art approaches to the design of capacitive sensors and sensing systems.

DESCRIPTION OF THE PREFERRED EMBODIMENT

For purposes of the present application, the applicants' invention will be described in the context of a relative humidity sensor. Although it is common to use a circuit including a capacitive sensor for sensing relative humidity, the invention is equally applicable to a variety of other devices in which a measurement is derived from the capacitance of a variable capacitance sensing element.

Figure 1:
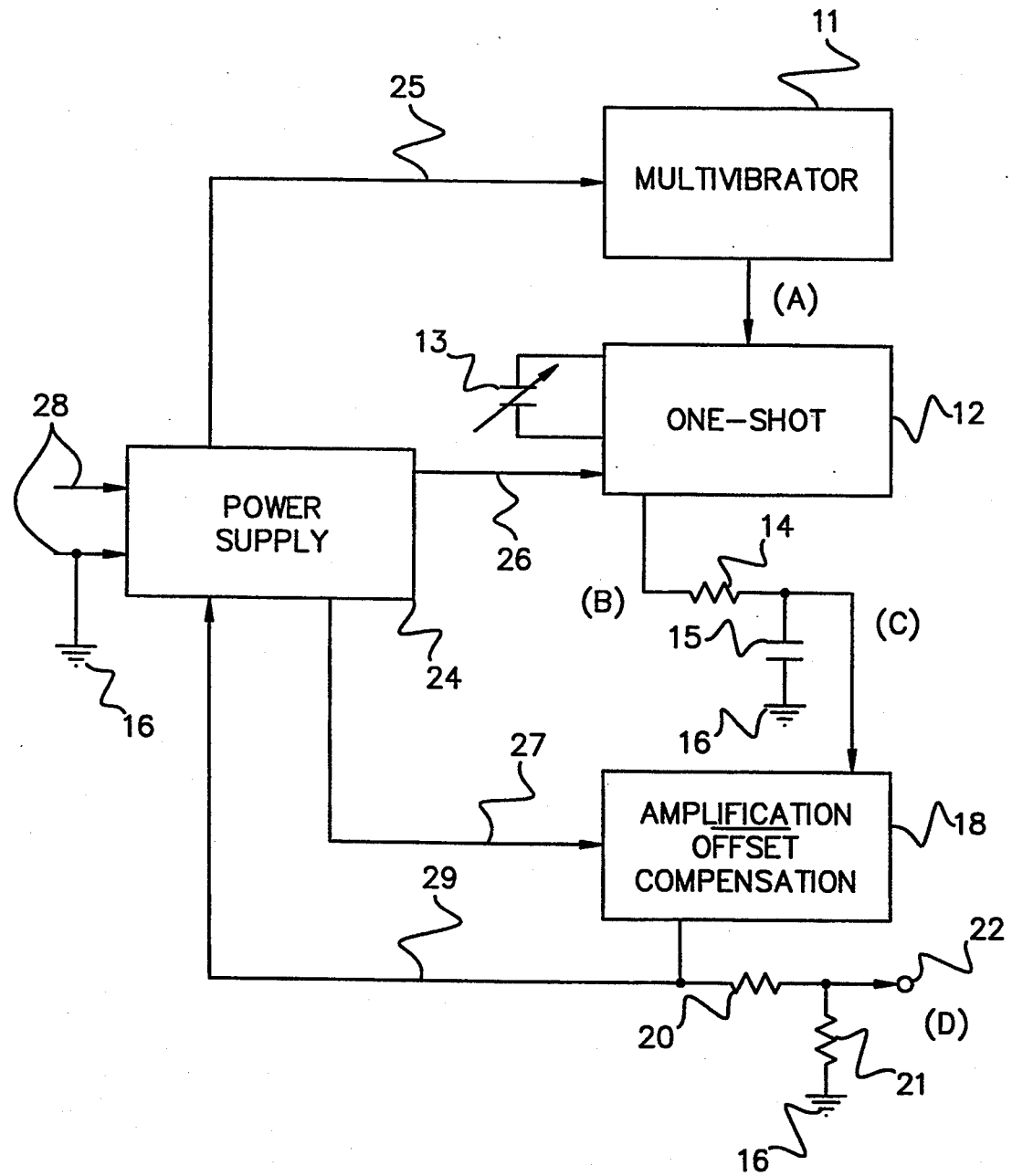
FIG. 1 is a functional block diagram of a capacitive measuring sensor circuit in accordance with the applicants' invention.
Figure 2A:
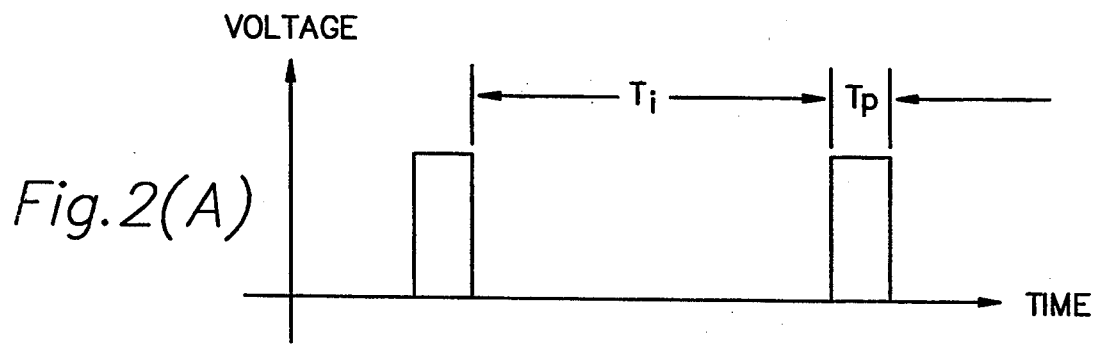
FIGS. 2(A) through 2(D) illustrate representative signals produced at indicated points in the circuit of FIG. 1.

In the block diagram of FIG. 1, reference numeral 11 identifies a multivibrator designed and operable to produce a train of pulses as shown in FIG. 2(A), each pulse having a duration $T_p$, and successive pulses being separated by an interval $T_i$. Multivibrator 11 is designed such that the interval between pulses is much longer than the pulse duration. Further, as will be described in detail hereinafter, multivibrator 11 is designed such that the interval between pulses can be varied.

Figure 2B:
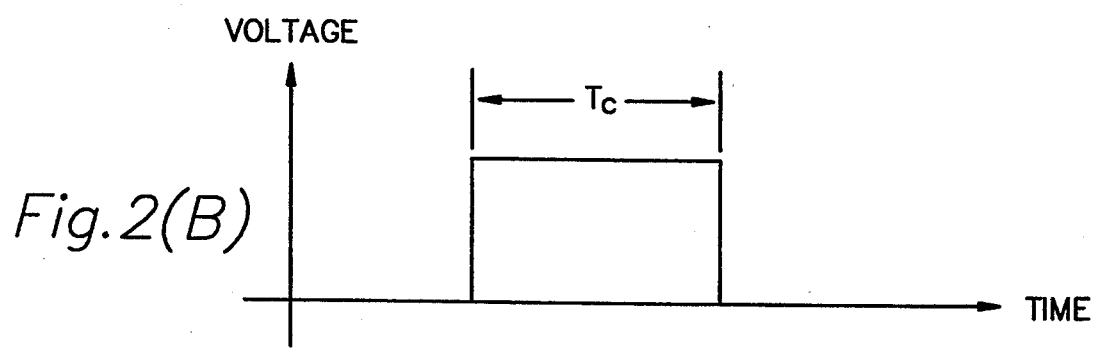

The output pulse train of multivibrator 11 is supplied to a one-shot circuit 12 or other bistable device which is adapted to produce a pulse whose leading edge is synchronized with the trailing edge of each pulse produced by the multivibrator. As shown in FIG. 2(B), the pulses produced by one-shot circuit 12 have a pulse duration $T_c$ which is directly proportional to the capacitance $C_s$ of a capacitive sensing element 13 whose capacitance varies in response to an environmental parameter, such as relative humidity.

Since capacitive sensing elements typically exhibit high (±20%) unit-to-unit variations in capacitance value at a predetermined humidity, it is necessary or desirable to provide convenient means for calibration so that reasonable uniformity between devices which incorporate the sensing elements can be achieved. For this purpose, the output pulse train of multivibrator 11 is variable between approximately 50,000 and 200,000 repetitions per second.

Since a common application for a humidity sensor of the present type may require installation of at least a portion of the circuit, e.g., the capacitive sensor, multivibrator and one-shot circuit, in a normally inaccessible air duct, and installation of the remaining circuitry, e.g., a power supply and signal processing circuitry, at a separate location, it is desirable that the operating repetition rate of the multivibrator be variable from the separate location. The applicants' circuit design advantageously permits such separation, as will be described hereinafter.

Figure 2C:
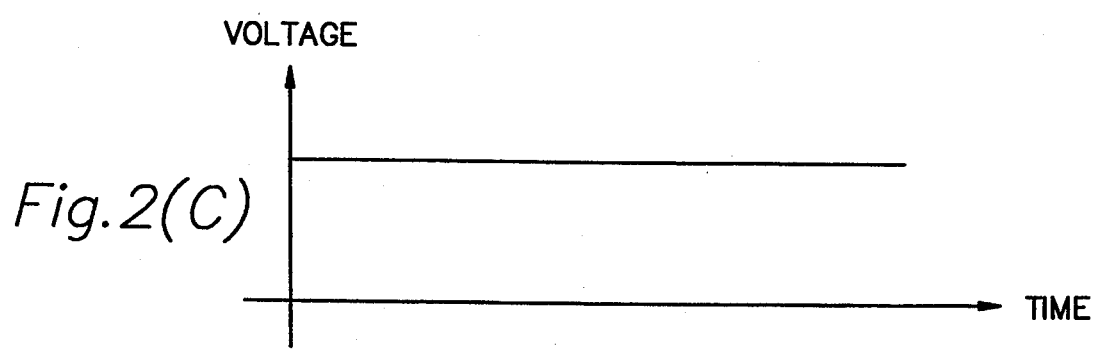
Figure 2D:
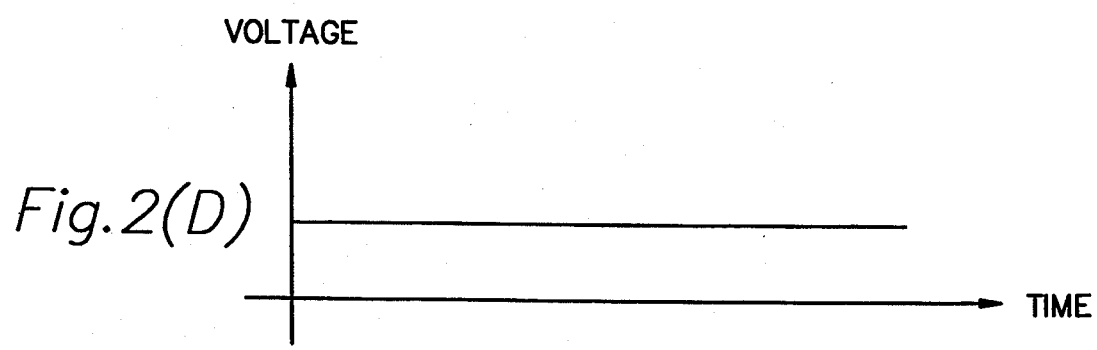

The output pulse train of one-shot circuit 12 is supplied to an integrator formed of a resistor 14 and a capacitor 15 connected in series between circuit 12 and a source 16 of ground or reference potential for the sensor circuit. The integrator functions to integrate the pulse train produced by one-shot circuit 12, and produce a voltage which is proportional to the time average of the pulse train voltage according to the expression, $T_c/(T_i+T_p)$, as shown in FIG. 2(C).

The voltage produced by the integrator is supplied to an amplification and offset compensation network 18 which, in part, functions to subtract a voltage from the voltage across capacitor 15, the value of the subtracted voltage preferably having the same value as the Voltage across capacitor 15 at 0% relative humidity. It follows from the foregoing that the subtracted voltage value determines the signal amplification necessary from network 18. In the preferred example, the humidity sensor circuit would produce a zero volt output signal for a 0% sensed relative humidity.

Furthermore, it is typically desired that the circuit output voltage range be standardized to a range of 0 to 1 volt over a measuring range of 0% to 100% relative humidity. This is achieved by means of a voltage divider comprising resistors 20 and 21 connected between the output of network 18 and ground 16, with the circuit output signal being produced at an output terminal 22 connected to the junction between the resistors. For output impedance matching purposes, resistors 20 and 21 may be chosen to provide a desired total resistance, such as 500 ohms.

As previously indicated, the operating repetition rate of multivibrator 11 can be varied to compensate for the non-linear relationship between the capacitance of sensing capacitor 13 and the sensed relative humidity. This is accomplished by varying the supply voltage to multivibrator 11 in response to the output voltage of amplification/offset compensation network 18. The supply voltage is provided by a power supply circuit 24 which supplies electrical power to multivibrator 11, one-shot circuit 12 and amplification/offset compensation network 18 over power conductors 25, 26 and 27 respectively. Power supply circuit 24 receives alternating electric current from an AC power source (not shown) over conductors 28. The AC voltage, for example, may be 24 volts. Power supply 24 is designed to produce a DC output voltage which varies in response to a control signal supplied from network 18 through a conductor 29. The DC supply voltage produced by power supply 24, for example, may vary from 5 volts to 7 volts over the intended range of measured relative humidities in order to compensate for the non-linear characteristic of capacitive sensor 13.

Figure 3:
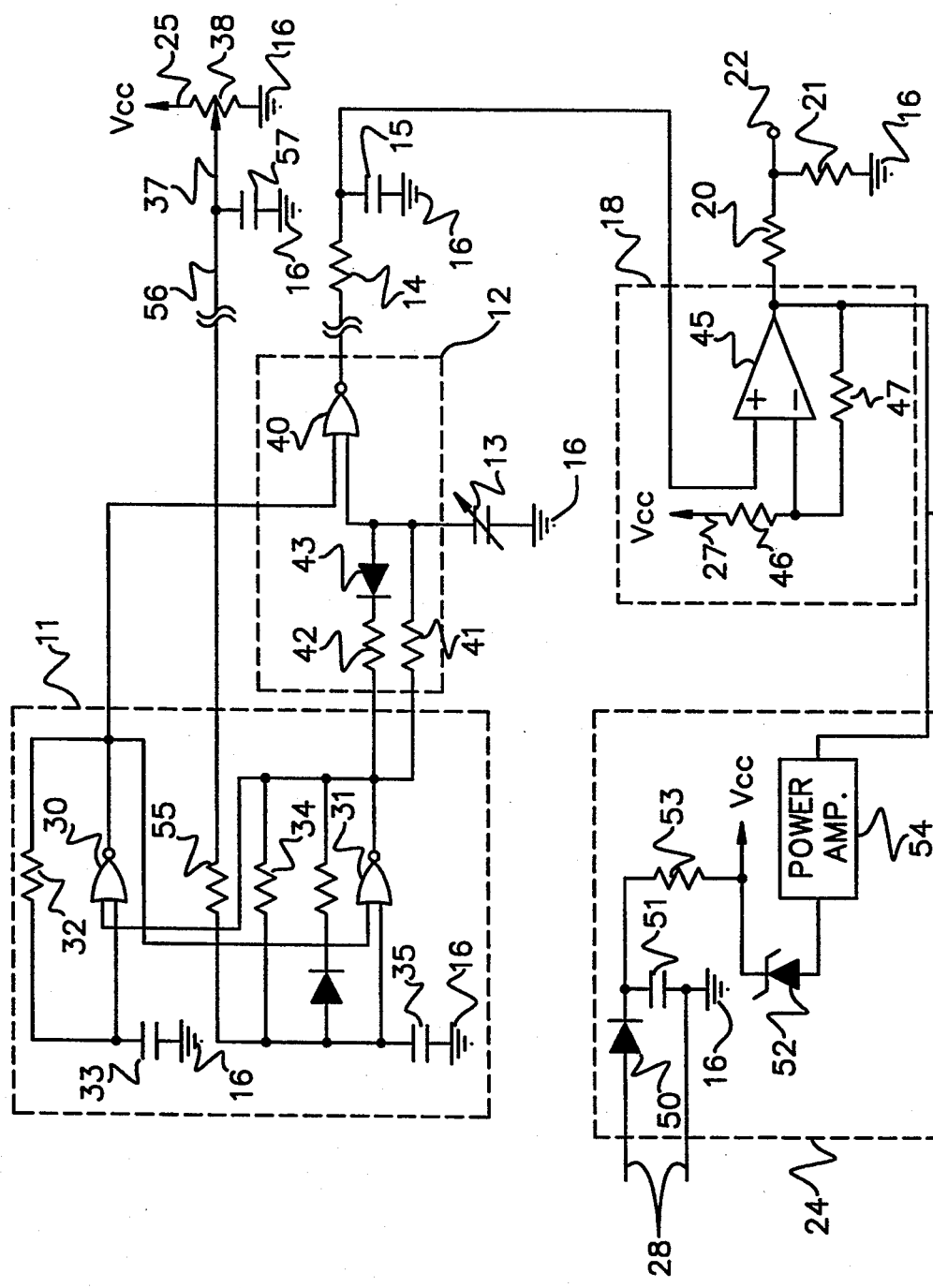
FIG. 3 is a circuit diagram of the circuit shown in block diagram form in FIG. 1.

In the detailed circuit diagram of FIG. 3, elements or features corresponding to those shown in FIG. 1 are identified by the same reference numerals. Multivibrator 11 is formed of two cross coupled NAND logic circuits 30 and 31 which are preferably of CMOS construction. The output of NAND circuit 30 is connected to one input thereof through an RC circuit formed of a resistor 32 and a capacitor 33, the time constant of which determines the multivibrator pulse duration $T_p$. Similarly, the output of NAND circuit 31 is connected to one input thereof through an RC circuit formed of a resistor 34 and a capacitor 35, the time constant of which determines the interval $T_i$ between pulses. Capacitors 33 and 35 are preferably NPO capacitors which resist the effects of aging and exhibit capacitances that are essentially independent of temperature.

Capacitor 35 is periodically charged at a rate depending on a charging voltage supplied through the wiper 37 of a potentiometer 38 connected to receive the DC output voltage of power supply 24. Thus, changing the position of wiper 37 varies the charging voltage supplied to capacitor 35 and the time required for the voltage thereacross to reach that sufficient to switch the output of NAND circuit 31. Accordingly, the operating repetition rate of multivibrator 11 and one-shot 12 can be controlled from potentiometer 38. As previously indicated, a variable operating repetition rate serves to compensate for the wide capacitance value tolerance (±20%) of capacitive sensor 13 which determines the duration $T_c$ of the pulses produced by one-shot circuit 12. By means of this adjustment, of which a more detailed explanation follows, the sensor circuits can be calibrated so as to provide unit-to-unit uniformity of response to relative humidity.

One-shot circuit 12 is formed of a NAND logic circuit 40 also preferably of CMOS construction. Thus, multivibrator 11 and one-shot circuit 12 are shown formed from logic gates of like construction. A first input of NAND circuit 40 is connected to the output of NAND circuit 30 in multivibrator 11. A second input of NAND circuit 40 is connected to ground 16 through capacitive sensor 13. The second input of NAND circuit 40 and capacitor 13 are also connected to the output of NAND circuit 31 through a charging path including a resistor 41, and through a discharging path including a resistor 42 and a diode 43 which is reversed biased during a high signal (pulse) at the output of NAND circuit 31. By changing the interval between successive pulses in the pulse train produced by NAND circuit 40, the voltage obtained through integrating the pulse train may be adjusted for any particular sensor 13 to provide the same sensor circuit output voltage for the same relative humidity. This results in the same calibrated value $T_c/T_i+T_p$ for all sensor circuits.

The voltage across capacitor 15 is supplied to the non-inverting input of an operational amplifier 45 in amplification and offset compensation circuit 18. The inverting input of operational amplifier 45 is connected to the voltage output terminal of power supply 24 through a resistor 46 and to the output of amplifier 45 through a resistor 47. By properly proportioning the resistances of resistors 46 and 47, an offset voltage of proper magnitude may be provided for producing an output signal of 0 volts in response to 0% relative humidity. Also, as previously indicated, the voltage divider comprising resistors 20 and 21, which is connected to the output of operational amplifier 45, serves to provide a standard range (0–1volt) for the humidity sensing circuit, and to provide for output impedance matching.

Power supply 24 produces a variable DC voltage Vcc for the remainder of the sensing circuit as follows. AC input voltage is supplied through a non-grounded conductor of AC input conductors 28, and is half wave rectified by means of a diode 50, the rectified voltage being filtered by a capacitor 51. The cathode of a Zener diode 52 is supplied with the voltage across capacitor 51 through a resistor 53. The voltage at the anode of Zener diode 52 is controlled from the output of operational amplifier 45 through a power amplifier 54. This results in a DC supply voltage of $Vcc = nV_f + V_{ref}$, were $V_f$ is the output voltage of operational amplifier 45, $V_{ref}$ is the voltage across Zener diode 52 and n is the amplification factor of power amplifier 54. Thus, the DC supply voltage corresponds to the sum of the reference voltage across diode 52 and a voltage proportional to the output voltage of amplifier 45 when diode 52 is reverse biased to above its breakdown voltage.

The factor n by which DC supply voltage Vcc must be increased with increasing value of the measured parameter depends on the relative decrease in sensitivity of sensing capacitor 13 to increasing value of the parameter, and on the value $T_c/(T_p + T_i)$. By properly selecting the amplification factor, of power amplifier 54, a linear response of a circuit to relative humidity can be achieved.

As previously indicated, charging of capacitor 35 in multivibrator 11 can be accelerated or retarded by appropriate positioning of wiper 37 of potentiometer 38. In particular, the charging of capacitor 35 during production of a pulse by NAND circuit 31 through resistor 34 is accelerated if wiper 37 is positioned to supply a higher voltage through resistor 55, and is retarded if wiper 37 is positioned to provide a lower voltage.

Since potentiometer 38 may be at a location separated from multivibrator 11, the properties of a conductor 56 which connects the locations, particularly the capacitance contributed thereby, must be taken into account. By providing compensation circuitry, such as a capacitor 57 whose capacitance is large compared to the capacitance of conductor 56, the effect of conductor 56 on circuit operation may be minimized.

In accordance with the forgoing description, the applicants have provided a unique circuit for evaluating the signal of a capacitive measuring sensor, the circuit having various advantages over previously known capacitive sensing circuits. Although a particular embodiment has been shown and described for a illustrative purposes, a number of variations and modifications will be apparent to those of ordinary skill in the relevant arts. It is not intended that coverage be limited to the embodiment shown, but only by the terms of the following claims.

The embodiments of the invention in which an exclusive property or right is claimed are defined as follows:

1. A circuit of the type having a sensing element whose capacitance varies with variations in an environmental parameter, a multivibrator for producing a pulse train whose repetition rate is independent of the environmental parameter and a bistable device whose switching operation is determined, at least in part, by the capacitance of the sensing element, wherein the improvement comprises:
   a controllable multivibrator designed to produce a pulse train having a periodic feature whose repetition rate is variable in response to the magnitude of a control signal supplied thereto;
   a one-shot circuit connected to receive the pulse train produced by said controllable multivibrator, and operable to produce an output pulse synchronized with the periodic feature of the multivibrator pulse train, said one-shot circuit further being connected to the sensing element, the pulses produced by said one-shot circuit having a pulse duration dependent on the capacitance of the sensing element;
   amplification means connected to receive the output pulses from said one-shot circuit, and operable to produce an output signal indicative of the value of the environmental parameter sensed by said sensing element;
   controllable power supply means designed to provide a supply voltage which is variable in response to variations in a control signal supplied thereto;
   means for supplying the output signal said evaluation means as the control signal to said controllable power supply means; and
   connecting means for furnishing a signal voltage proportional to the supply voltage as the control signal to said controllable multivibrator.

2. The circuit of claim 1 wherein said amplification means comprises:
   a differential amplifier having input terminal means and an output terminal at which is produced an output voltage signal indicative of voltage signals supplied to the input terminal means; and
   an integrator circuit connected to receive the output pulses produced by said one-shot circuit and connected to the input terminal means of said differential amplifier to supply thereto an input voltage signal indicative of the time average voltage value of the output pulses produced by said one-shot circuit.

3. The circuit of claim 2 wherein:
   the input terminal means of said differential amplifier includes non-inverting and inverting input terminals;
   said integrator circuit is connected to the non-inverting input terminal of said differential amplifier; and
   the inverting input terminal of said differential amplifier is supplied with a voltage derived from the supply voltage and the output signal of said evaluation means.

4. The circuit of claim 3 wherein said multivibrator comprises first and second cross couple logic gates, each having an input terminal connected to be impressed with the voltage across a separate capacitor, the capacitors associated with said first and second logic gates being connected to receive charging current from output terminals of the first and second logic gates respectively, the capacitor associated with said first logic gate further being connected to receive charging current through said connecting means, whereby said controllable multivibrator produces a train of pulses whose pulse duration is determined by charging of the capacitor associated with said second logic gate and the interval between pulses is determined by charging of the capacitor associated with said first logic gate.

5. The circuit of claim 4 wherein said multivibrator produces a pulse train in which the duration of the pulses is small with respect to the interval between successive pulses.

6. The circuit of claim 5 wherein the logic gates in said multivibrator and said one-shot circuit are CMOS NAND logic gates.

7. The circuit of claim 6 wherein:
said controllable power supply means includes a control terminal, and produces a supply voltage at the output terminal thereof in response to increases in a voltage supplied to the control terminal thereof, the control terminal being connected to the output terminal of said differential amplifier;
said multivibrator includes voltage responsive means which causes the interval between pulses in the pulse train produced by the multivibrator to decrease as a voltage supplied thereto increases; and
said connecting means is operable to furnish the supply voltage provided by said controllable power supply means to the multivibrator, whereby the supply voltage in caused to increase as the output signal voltage of said differential amplifier increases to provide compensation for a sensor element whose sensitivity decreases as its capacitance value increases.

8. The circuit of claim 7 wherein said power supply produces a supply voltage corresponding to the sum of a reference voltage and a voltage proportioned to the output voltage of said differential amplifier.

9. The circuit of claim 8 wherein:
said multivibrator and said one-shot circuit are located at a first location;
said amplification circuit and said power supply are located at a second location remote from the first location; and
said multivibrator and said one-shot circuit at the first location are connected to said amplification circuit and said power supply at the second location through electrical conductor means.

10. The circuit of claim 9 wherein:
said electrical conductor means is characterized by properties which could affect the output voltage produced by said differential amplifier; and
compensation circuitry is provided, said compensation circuitry being associated with said electrical conductor means, and being operable to minimize the effect of the properties of said electrical conductor means on the output voltage produced by said differential amplifier.

* * * * *